US006202855B1

(12) United States Patent
Omtveit et al.

(10) Patent No.: US 6,202,855 B1
(45) Date of Patent: Mar. 20, 2001

(54) PROCESS FOR THE SELECTION OF PARTICLES OF A PRESELECTED SIZE FROM A PARTICULATE PHARMACEUTICAL PRODUCT

(75) Inventors: Tore Omtveit; Bjørn Haugseter, both of Oslo (NO)

(73) Assignee: Nycomed Imaging AS, Oslo (NO)

( * ) Notice: Subject to any disclaimer, the term of this patent is extended or adjusted under 35 U.S.C. 154(b) by 0 days.

(21) Appl. No.: 09/459,986

(22) Filed: Dec. 14, 1999

Related U.S. Application Data

(63) Continuation of application No. PCT/GB98/01976, filed on Jul. 3, 1998.
(60) Provisional application No. 60/053,934, filed on Jul. 28, 1997, and provisional application No. 60/064,306, filed on Nov. 5, 1997.

(30) Foreign Application Priority Data

Jul. 4, 1997 (GB) .................................... 9714170
Aug. 13, 1997 (GB) .................................... 9717150

(51) Int. Cl.$^7$ ........................................ B03B 5/28
(52) U.S. Cl. ..................... 209/172; 209/172.5; 209/173; 209/155
(58) Field of Search ..................... 209/155, 172, 209/172.5, 173, 3; 428/402

(56) References Cited

U.S. PATENT DOCUMENTS

| 4,732,664 | 3/1988 | Solari et al. . |
| 4,744,228 | 5/1988 | Goldberg . |
| 4,750,992 | 6/1988 | Romine . |

FOREIGN PATENT DOCUMENTS

| 0 277 704 | 8/1988 | (WO) . |
| 0 458 745 | 11/1991 | (WO) . |
| 0 633 030 | 1/1995 | (WO) . |

OTHER PUBLICATIONS

Patent Abstracts of Japan, 004:026 (C–001), Mar. 6, 1980 & JP 55 001890 A (Toyo Soda Mfg Co. Ltd.), Jan. 9, 1980.

*Primary Examiner*—Donald P. Walsh
*Assistant Examiner*—Jonathan R. Miller
(74) *Attorney, Agent, or Firm*—Bacon & Thomas (57) ABSTRACT

An invention provides a process for the selection from a particulate pharmaceutical product of particles of a preselected size, said process comprising (i) obtaining a substantially homogeneous suspension of said particulate pharmaceutical product in a fluid suspension medium which is immiscible with said product and is of different density to said product, (ii) carrying out a size selection procedure to set an effective lower or upper size limit on the articles in the final particulate product, wherein step (ii) comprises either allowing said suspension to settle for a predetermined period, separating said suspension into a first and second component in a predetermined volume ratio, said first component deriving from an upper layer of said suspension and said second component deriving from a lower layer of said suspension, adding further suspension medium to said first component where said medium is more dense than the pharmaceutical product or to said second component where said medium is less dense than the pharmaceutical product and mixing to produce a substantially homogeneous suspension of particulate pharmaceutical product in said fluid suspension medium, and repeating steps at least once, optionally omitting the last repeat of step whereby to set an effective lower size limit on the particles in the final particulate product, or (viii) allowing said suspension to settle for a predetermined period, (ix) separating said suspension into a third and a fourth component in a second predetermined volume ratio, said third component deriving from an upper layer of said suspension and said fourth component deriving from a lower layer of said suspension, and retaining said third component where said medium is less dense than the pharmaceutical product or said fourth component where said medium is more dense than said product, whereby said second predetermined volume ratio is such as to set an effective upper size limit on the particles in the retained component.

7 Claims, 10 Drawing Sheets

FIG. 5

PROCESS FOR THE SELECTION OF PARTICLES OF A PRESELECTED SIZE FROM A PARTICULATE PHARMACEUTICAL PRODUCT

This application is a continuation of pending international application number PCT/GB98/01976 filed Jul. 3, 1998 (of which the entire disclosure of the pending, prior application is hereby incorporated by reference), which itself is a continuation-in-part of U.S. provisional application number 60/053,934 filed Jul. 28, 1997 and also a continuation-in-part of U.S. provisional application number 60/064,306 filed Nov. 5, 1997.

This invention relates to a process for size selection of particulate pharmaceuticals, in particular contrast agents for use in diagnostic imaging procedures such as for example magnetic resonance, X-ray (eg. CT), scintigraphy and ultrasound imaging.

In many diagnostic imaging modalities substances, contrast agents, are administered to the subject to enhance image contrast, for example to facilitate differentiation between different tissues or organs or between healthy and unhealthy tissues. While particulate materials have long been used as contrast agents for the gastrointestinal tract, more recently the parenteral administration of particulate contrast agents has been proposed.

While for administration into the GI tract the particle size and size distribution has not generally been considered to be particularly important, the same is not true of parenterally administered particulate agents, for example because of the risk of embolisation by overly large particles.

Accordingly in the preparation of particulate contrast agents for parenteral administration there is a need to ensure that the mean particle size and the particle size distribution are within desired limits.

The present invention provides a particularly straightforward solution to this problem.

Thus viewed from one aspect the present invention provides a process for the selection from a particulate pharmaceutical product of particles of a preselected size (eg. a substantially monodisperse fraction), said process comprising (i) obtaining a substantially homogeneous suspension of said particulate pharmaceutical product in a fluid suspension medium which is immiscible with said product and is of different density to said product, (ii) carrying out a size selection procedure to set an effective lower or upper size limit on the particles in the final particulate product, and (iii) where required carrying out a further size selection procedure to produce a particulate product containing particles of the preselected size, wherein step (ii) comprises either (iv) allowing said suspension to settle for a predetermined period, (v) separating said suspension into a first and a second component in a predetermined volume ratio, said first component deriving from an upper layer of said suspension and said second component deriving from a lower layer of said suspension, (vi) adding further suspension medium to said first component where said medium is more dense than the pharmaceutical product or to said second component where said medium is less dense than the pharmaceutical product and mixing to produce a substantially homogeneous suspension of particulate pharmaceutical product in said fluid suspension medium, and (vii) repeating steps (iv) to (vi) at least once, optionally omitting the last repeat of step (vi), adding the fluid suspension medium in the repeat of step (vi) to the first component or the second component where the substantially homogeneous suspension produced in the first operation of step (vi) derives from the first component or the second component respectively, whereby to set an effective lower size limit on the particles in the final particulate product, or (viii) allowing said suspension to settle for a predetermined period, (ix) separating said suspension into a third and a fourth component in a second predetermined volume ratio, said third component deriving from an upper layer of said suspension and said fourth component deriving from a lower layer of said suspension, and retaining said third component where said medium is less dense than the pharmaceutical product or said fourth component where said medium is more dense than said product, whereby said second predetermined volume ratio is such as to set an effective upper size limit on the particles in the retained component, and optionally (x) adding further suspension medium to the non-retained component and mixing to produce a substantially homogeneous suspension, (xi) repeating steps (viii), (ix) and (x) one or more times, optionally omitting the last repeat of step (x), and collecting the retained components from step (ix) and repeats thereof.

Where step (ii) is effected so as to set a lower size limit, ie. by operation of steps (iv) to (vii), step (iii) may advantageously comprise operation of steps (viii) to (xi) after a final repetition of step (vi).

In effect therefore the process of the invention may involve removal of particles below a desired lower size limit from a polydisperse particulate, followed by removal and retention of particles below a desired upper size limit from the remaining particulate mixture. The retained particulate mixture then contains particles within a desired size range. Alternatively the removal of over-sized particles may be effected analogously to steps (viii) to (xi) prior to or during removal of under-sized particles by steps (iv) to (vii).

The starting material for the process of the invention may thus be a particulate product in which the upper or the lower size limit or neither the upper nor the lower size limit has been set. While the process may be used to set both size limits, it is especially preferred to use a starting material for which the upper size limit has been set, e.g. by the removal of over-sized particles or by the use of a particle creation technique which does not produce over-sized particles, e.g. the use of a rotor-stator for the production of particles which are vesicles or emulsion droplets. Alternatively the process of the invention may be used simply to set a lower particle size limit for a particle product in which the incidence of over-sized particles is acceptably low, or from which the over-sized particles may subsequently be removed, e.g. by skimming or decanting. It will be noted that while steps (viii) to (xi) can be used to remove essentially all over-sized particles, the extent to which under-sized particles are removed by steps (iv) to (vii) will depend upon the number of repetitions. For this reason the lower size limit is referred to as an "effective" size limit.

The use of a rotor-stator to generate a particle mixture from which under-sized particles are removed using the process of the invention is novel and especially advantageous and forms a further aspect of the invention. Viewed from this aspect the invention provides a process for the production of a particulate pharmaceutical product, said process comprising:

(A) generating with a rotor-stator a particulate pharmaceutical product, (B) obtaining a substantially homogeneous suspension of the particulate product generated in step (A) in a fluid suspension medium which is immiscible with and of different density to the particulate product, (C) allowing said suspension to settle for a predetermined period, (D) separating said suspension into a first and a second component in a predetermined volume ratio, said first component deriving from an upper layer of said suspension and said second component deriving from a lower layer of said suspension, (E) adding further suspension medium to said first component where said medium is more dense than the pharmaceutical product or to said second component where said medium is less dense than the pharmaceutical product and mixing to produce a substantially homogeneous suspension of particulate pharmaceutical product in said fluid suspension medium, and (F) repeating steps (C) to (E) at least once, optionally omitting the last repeat of step (E), adding the fluid suspension medium in the repeat of step (E) to the first component or the second component where the substantially homogeneous suspension produced in the first operation of step (E) derives from the first component or the second component respectively, whereby to set an effective lower size limit on the particles in the final particulate product.

The particulate product of the process of the invention can subsequently be concentrated and if desired dried to yield a size selected powder, suspension or dispersion.

Where the particulate material is less dense than the fluid suspension medium, following homogenisation of the suspension, eg. by stirring, the particulate will settle out by flotation rising towards the top of the suspension. Accordingly as used herein the terms settle, settling and settlement, where the context admits, are deemed to cover settling upwards by flotation as well as settling downwards.

The rate of rise of the particles during settling is dependent on particle size with smaller particles rising more slowly. Accordingly the level at which the subsequent split between upper and lower components is made is set to correspond to the level below which, at the time the split is made, substantially only particles below the desired size limit remain. Following a single settling step like this, the upper component will contain particles below the size limit but these will be removed in the subsequent repetitions. The number of repetitions carried out will depend on the degree to which removal of the smaller particles is required. In steps (iv) to (vii) (or (C) to (F)) of the process, in which particles below the desired lower particle size limit are removed, it will generally be desirable to carry out 2 to 100, preferably 3 to 30, more preferably 5 to 15 settling out and separation steps. In steps (viii) to (ix) of the process, in which the particles below the desired upper size limit are removed and retained, a single settling out and separation step may be sufficient although to maximise yield a plurality, eg. 2 to 100, preferably 3 to 30, more preferably 5 to 15 settling out and separation steps may be effected.

The rejected components will preferably be collected. The particles below the desired size limit collected in steps (iv) to (vii) (or (C) to (F)) of the process may be recovered and the pharmaceutical material reused, eg. to produce larger particles for separation according to the process of the invention. The larger particles again may be recovered and reused, eg. after size reduction, for example milling for solid particles or extrusion through pores of appropriate size for liquid or semi-solid particles or vesicles (eg. micelles, liposomes, stabilised microbubbles, microballoons, etc).

The time period for which settling is allowed to proceed for a predetermined proportion of fluid to be withdrawn in order to obtain a specific size limit cut off can be calculated as follows:

The rate of rise of particles in a liquid (when the particles are less dense than the liquid) may be determined by Stoke's law (see: B. S. Massey: Mechanics of Fluids; 4th edition, van Nostrand Reinhold (1979), page 159):

$$u = \frac{d^2(\rho_L - \rho_P)g}{18\mu} \quad \text{(I)}$$

(where $\rho_L$=density of liquid
$\rho_P$=density of particle
$\mu$=coefficient of absolute viscosity
d=desired cut-off diameter
g=gravitational acceleration, and
u=rising velocity of particle of cut-off size).

The time required for a particle to rise from the bottom of the settlement container to the predetermined drainage height is given by the equation $$t = s/u \quad \text{(II)}$$

(where u is as defined above,
s=predetermined drainage height, and
t=flotation time),
and for particles of a given diameter, the maximum time needed for complete recovery (i.e. for all such particles to enter that volume which is recovered) is found by combining equations (I) and (II), to give equation (III):

$$t = \frac{18 \cdot S \cdot \mu}{d^2 \cdot (\rho_L - \rho_P) \cdot g} \quad \text{(III)}$$

Thus, for a settling time t, all particles above size d have passed the drainage height border.

Where the particles are more dense than the fluid suspension medium, the smaller particles settle out by sedimentation more slowly than the larger particles and thus the first part of the process involves removal (possibly for reuse as discussed above) of the upper component after the settling out while the second part of the process involves collection of the upper component after settling out as it is then the upper component that contains the particles which have sizes in the desired range. Otherwise in terms of repetitions, concentration, drying, reuse etc. the process is carried out as described above for the less dense particulate.

Besides gravity, which is reinforceable using centrifugation, other force fields may be used in the separation process of the invention, eg. magnetic or electrostatic fields may be used for separation of particles which move within the fluid suspension medium under the action of such fields, for example ferromagnetic, ferrimagnetic, superparamagnetic and electrically charged particles. In this event the separation should be along a boundary perpendicular to the field direction and the field direction need not be, but preferably is, vertical.

The fluid suspension medium used in the process of the invention may be a gas or liquid. Generally it will be a material which has a different density to that of the particulate product, a material in which the particulate product is insoluble, and a material which does not react with the particulate product. The medium may contain stabilizing agents such as pH regulators, viscosity modifiers, ionic strength or osmolality modifiers, or agents which are capable of modifying particle separation (e.g. flotation) rates. Preferably the medium will be a physiologically tolerable liquid, such as water or an aqueous solution (eg. containing materials such as salts, sugars, polysaccharides, viscosity modifiers, pH adjusting agents, osmolality modifiers, surfactants, stabilisers, antioxidants, antifoaming agents, cryoprotectants, lyoprotectants, etc.).

The processes of the invention may be used to produce a particulate material which is relatively free of under- and/or over-sized particles and generally the product of the process will be a suspension of the selected particles. Such suspensions may be concentrated by allowing the particles to settle and removing an upper or lower portion of the suspension medium (ie. removing a lower portion where the particles are less dense than the suspension medium, etc). Desirably the time for which settling is allowed to take place and the volume of suspension medium removed are such that essentially none of the particles of desired size are removed; however the time and volume do not have to be set so accurately so that they correspond to a desired particle size cut-off as in the process of the invention.

The process of the invention is desirably carried out using a settling and separation chamber which has vertical walls and a horizontal base with fluid withdrawal outlets in the base. The chamber must be sterilisable since the particulate is a pharmaceutical product. Advantageously the chamber is equipped with stirring means, preferably having one or more vertical blades rotatable about a vertical axis. Such apparatus is novel and forms a further aspect of the invention.

Thus viewed from a further aspect the invention provides a particulate pharmaceutical separation apparatus comprising a sterilizable separation chamber, stirring means disposed within said chamber and outlet means for removing fluid from the base of said chamber, wherein the side walls of said chamber are vertical and the base of said chamber is horizontal and wherein the base of said chamber contains a plurality of fluid outlet means openable to allow fluid to be withdrawn from said chamber.

To facilitate drainage, the horizontal base of the separation apparatus may desirably be slightly off true-horizontal, e.g. at an angle of up to 5°, preferably 1° to 3.5°, especially 2.8°. The term horizontal as used herein includes such slightly off true-horizontal orientations.

The apparatus may, but desirably does not, have off true-vertical side walls. However the side walls should not taper inwards along the direction of separation, ie. if particle density is less than that of the suspending medium, the side walls may taper outwardly in the upwards direction.

The fluid outlets are preferably coupled to conduit means for leading the fluid that is drawn off to tanks for storage or reuse. Particularly preferably such conduit means are provided with on-line or off-line size measurement means, such as for example near infrared spectroscopy apparatus or laser particle size determination apparatus, and valve means so that flow from the chamber may be halted (and if required redirected) if the measurement means detects particles in the outflow above (or below) a predetermined size.

The measurement means and the valve means may be operated under computer control and indeed the entire operation of the apparatus (eg. filling, stirring, opening of the outlet means, closing of outlet means, introduction of fresh suspension medium, stirring, etc) may be controlled by a computer.

The side walls and base of the separation chamber should be smooth and preferably should meet at a sharp 90° junction. The outlet means should be disposed uniformly in the base and each conveniently has an area of 1 $mm^2$ to 10 $cm^2$, preferably 5 $mm^2$ to 5 $cm^2$, depending for example upon whether the separation chamber is of laboratory or process plant scale. Desirably the chamber is cylindrical with a width of 5 cm to 2.5 m, especially 0.2 to 2 m, more especially 0.8 to 1.5 m and a height permitting a fluid depth of 3 to 100 cm, preferably 4 to 50 cm, particularly 5 to 20 cm. For particles of 1 to 10 $\mu$m diameter, fluid depths of 5 to 20 cm are preferred; for particles of larger diameter, eg. 30 to 50 $\mu$m, greater fluid depths are preferred, eg. 10 to 50 cm. The side walls and base may for example be of glass, stainless steel, or sterilisable plastics, eg. Perspex. It may be desirable for at least part of the side walls to be transparent, or for the top, bottom or side walls to contain an inspection window, so that the settling process may be monitored through the walls.

In another embodiment, the outlet apertures may be positioned evenly distributed over the base of the separation chamber in the form of two multiply apertured plates, movable, eg. rotatable, relative to each other to bring apertures in the two plates into or out of line, ie. into aperture-fully open and aperture-fully closed configurations, optionally with intermediate part-open configurations being available to allow a continuous or stepwise transition from the fully-open to the fully-closed configurations. In this embodiment, both plates may be movable or alternatively one may be static with the second being movable.

The outlet means may be opened and closed by individual valve means or alternatively an apertured plate in the base of the chamber may be moved to open or close the outlets, eg. by rotation of an apertured disc to bring the apertures into registry with the outlet means.

Two or more separation chambers may be present in the apparatus of the invention so that where separation is to be repeated on the component drawn out of one chamber it can be effected in another so allowing the first chamber to be used in a new run of the process of the invention.

Desirably, the separation process takes place under controlled temperature conditions and thus the apparatus of the invention is preferably provided with means for monitoring and if required adjusting the temperature of the suspensions and the suspension medium, e.g. the separation chamber may be provided with a thermostat controlled heating or cooling jacket, and the feeder tanks and/or outlet tanks may be provided with temperature controls, again for example thermostat controlled heating or cooling jackets. Typically, such temperature control means might allow the process to be carried out at a temperature in the range 0 to 30° C., preferably 5 to 15° C., with the fluids mixing in the separation chamber being at the desired temperature for the separation step at the time that they are mixed.

Where fresh suspensions medium is added into the separation chamber during operation of the process of the invention, this is desirably achieved by spraying from above as this reduces undesirable foaming.

The process of the invention is applicable to all pharmaceutical particulates but is especially applicable to diagnostic contrast agents and/or vesicles, eg. liposomes, micelles, microballoons, emulsion droplets and stabilised microbubbles. The process allows the particles to be size separated without the mechanical stresses experienced in milling, extrusion or other mechanical grading techniques. It is particularly applicable to ultrasound contrast agents in the form of gas or gas-precursor containing vesicles. By gas or gas-precursor is meant a material or mixture of materials which is gaseous at body temperature (37° C.), eg. air, nitrogen, carbon dioxide or fluorinated materials such as $SF_6$ or perfluoroalkanes, eg. perfluoropentane and perfluorobutane. Thus for example the process may be used with the products of WO97/29783 (Nycomed), EP-A-77752 (Schering), WO91/15244, EP-A-458745 (Bracco), WO94/09829 (Sintetica), WO98/17324 (Nycomed) as well as the products known as Albunex, Cavisomes, NC100100, FS069 (Optison) and BR-1.

Where the process of the invention involves particle generation using a rotor-stator, this may be effected as for example is described in the examples of WO97/29783. Thus a rotor-stator may be used to generate particles from a liquid containing an immiscible component, e.g. a second liquid or a lipid or lipid mixture or other membrane forming material, and optionally a gas, gas mixture or gas precursor (by gas and gas mixture are included materials which are gaseous at 37° C.). Such particles may take the form of emulsion droplets (which can be surface-stabilized to prevent agglomeration) or vesicles (e.g. micelles and liposomes), in particular gas-containing vesicles. Rotor-stators capable of use to produce particulate pharmaceutical products in this way are available commercially.

The process of the invention enables a substantially monodisperse particle mixture to be separated out from a polydisperse mixture. For injectable pharmaceuticals this is important as removal of the over large particles reduces the risk of embolus formation. Since under-sized particles, especially contrast agent particles, represent a large wastage of the drug material, the process of the invention by allowing re-use and recycling of the drug material allows drug material wastage to be considerably reduced. Thus for example with gas-containing vesicles the gas can be removed from the membrane material in the non-selected components under reduced pressure or by mechanical rupture of the vesicle membrane and both can be re-used for production of new gas-containing vesicles.

Substantially monodisperse micron sized (eg. at least 85% by particle number being within 1 $\mu$m of the mean size, for example a size in the range 1 to 5 $\mu$m (for example 3±1 $\mu$m)) gas or gas-precursor containing vesicles are novel and form a further aspect of the invention. They are useful since particle size affects echogenicity and is affected by physiological environment. Accordingly such substantially monodisperse particles may be used to monitor changes in their physiological environment. Viewed from this aspect therefore the invention provides an ultrasound contrast medium comprising a physiologically acceptable liquid carrier medium containing a substantially monodisperse plurality of microparticles which are or in vivo are echogenic.

The invention will be described further with reference to the following non-limiting Examples and to the accompanying drawings, in which.

Figure 1:
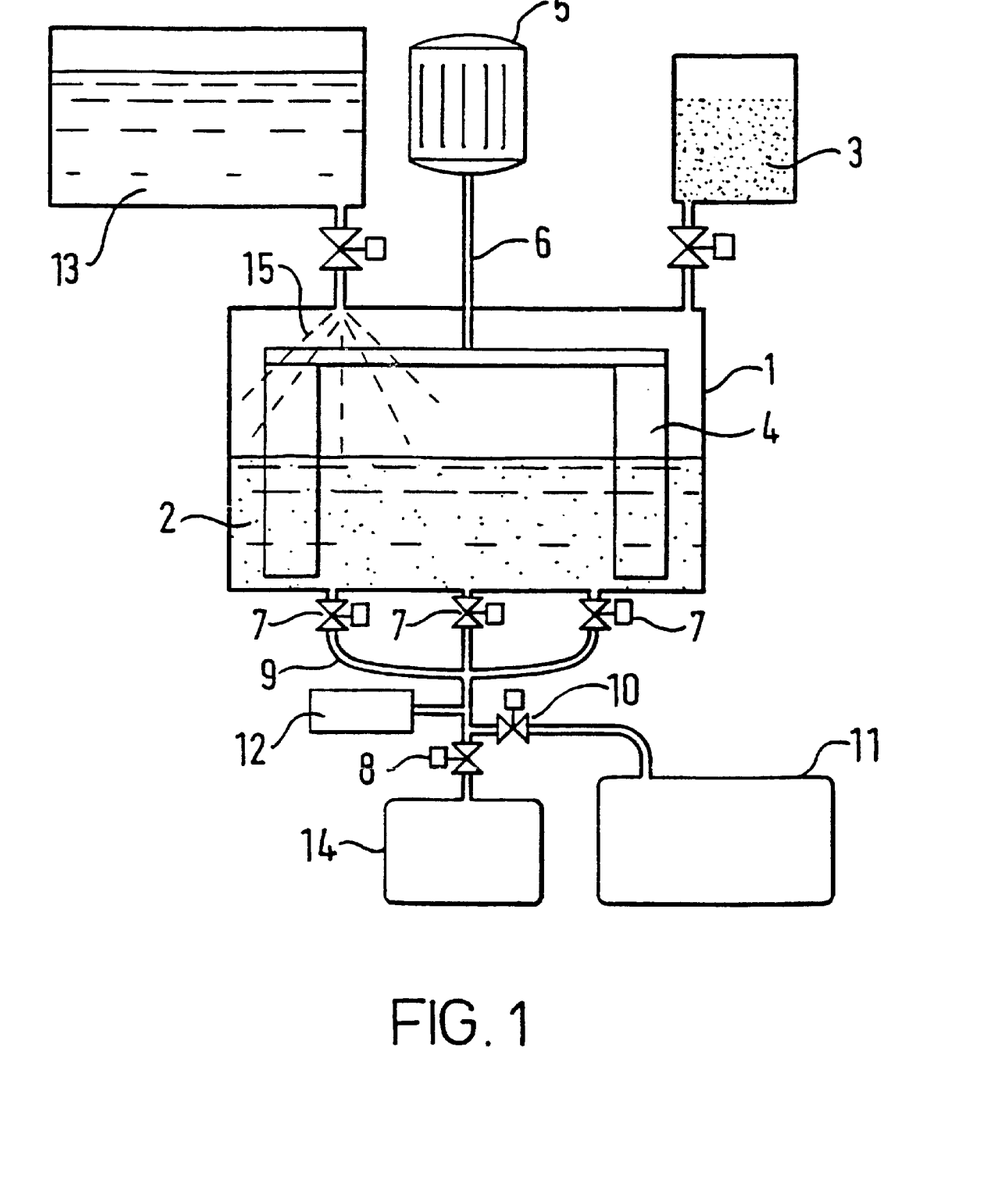
FIG. 1 is a schematic drawing of an apparatus according to the invention.

Referring to FIG. 1, there is shown a separation chamber 1 containing a pre-set volume of fluid suspension 2 introduced from particulate reservoir 3. This suspension is homogenized by rotation of vertical stirrer blades 4 under the action of stirrer motor 5 and stirrer shaft 6. The stirrer is then turned off and the suspension allowed to settle for a pre-determined time. Valves 7 in the base of chamber 1 are opened to allow the bottom layer of the suspension to flow into conduit 9 and valve 10 and thence to holding tank 11.

The flow through conduit 9 is monitored by laser apparatus 12 and flow is terminated by closure of valves 7 and 10 either after a pre-set time or when particles above a pre-set size are detected by laser apparatus 12. Further suspension medium is then added into chamber 1 from reservoir 13 through spray outlet 15. The mixture in chamber 1 is then agitated by the stirrer. The stirrer is switched off and the settlement, withdrawal, and refilling, etc. is repeated several times. The chamber is again refilled from reservoir 13 through spray outlet 15. The mixture is again stirred, the stirrer is switched off and, after a pre-set time, valves 7 and 8 are opened to allow fluid to pass into receiving tank 14. Flow is terminated by closure of valves 7 and 8 after a preset time or when laser apparatus 12 detects particles above the desired upper particle size limit. The suspension in chamber 1 is again stirred, the stirrer is switched off and after a preset time fluid is drawn off into receiving tank 14 as above. This is repeated several times and then the contents of tank 14 are taken for further processing, eg. concentration by flotation and drainage, and the contents of chamber 1 and holding tank 11 are removed for recycling.

Clearly, the depth and width of the separation chamber, number and size of the outlet apertures, and settling time and removal volume are factors that can be varied to optimize various aspects of the process. Thus greater depth and longer settling times allow a sharper size cut-off (and thus to remove ultra small particles it may be desirable to have one or more settlement steps operated for a longer time period), a wider chamber and increased numbers and reduced sizes of outlets reduces mixing during fluid removal, but deeper chambers and longer settlement times increase process duration.

The apparatus may be calibrated by withdrawing samples at various settlement times and depths within the fluid in the chamber and analysing their particle size distributions. In this way appropriate settling times and withdrawal volumes may be determined.

Figure 2:
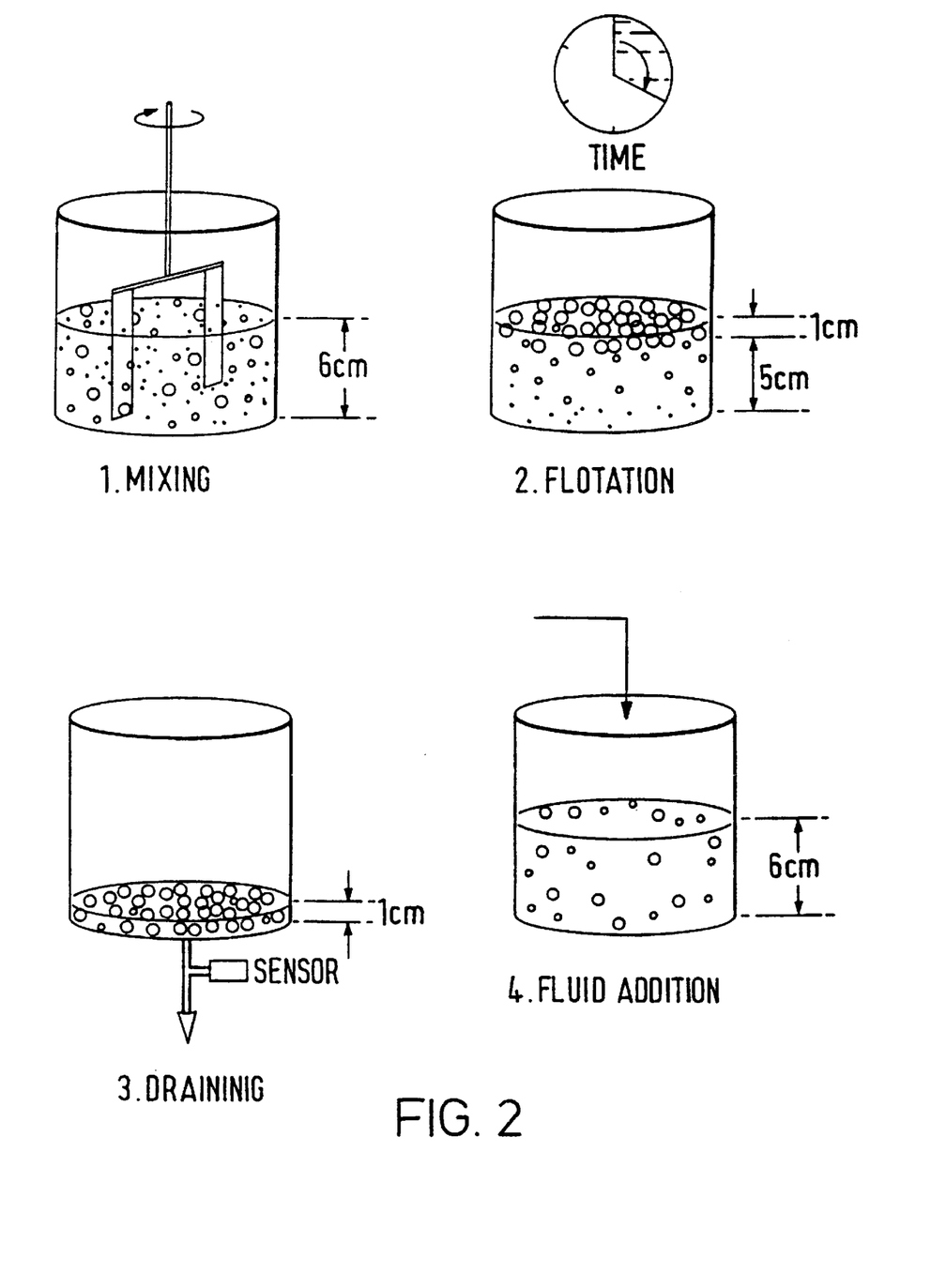
FIG. 2 is a schematic drawing showing the operation of the process of the invention.
Figure 3A:
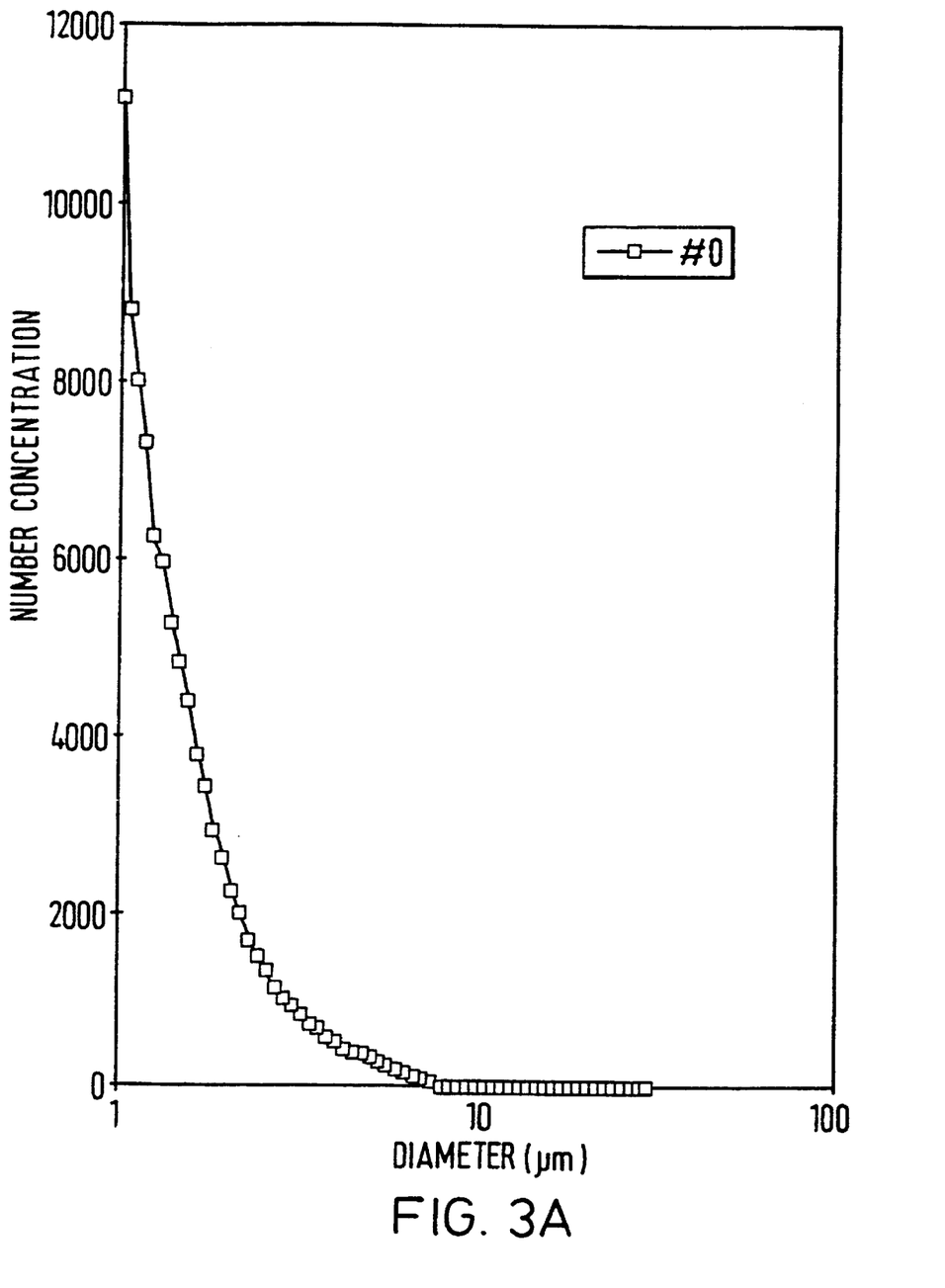
FIGS. 3A, 3B, 3C, 3D, 3E and 3F are a series of graphs showing the size distributions of a particulate mixture before the process of the invention and after respectively 1, 3, 5, 7 and 9 separation cycles to remove particles below the desired size limit.
Figure 3B:
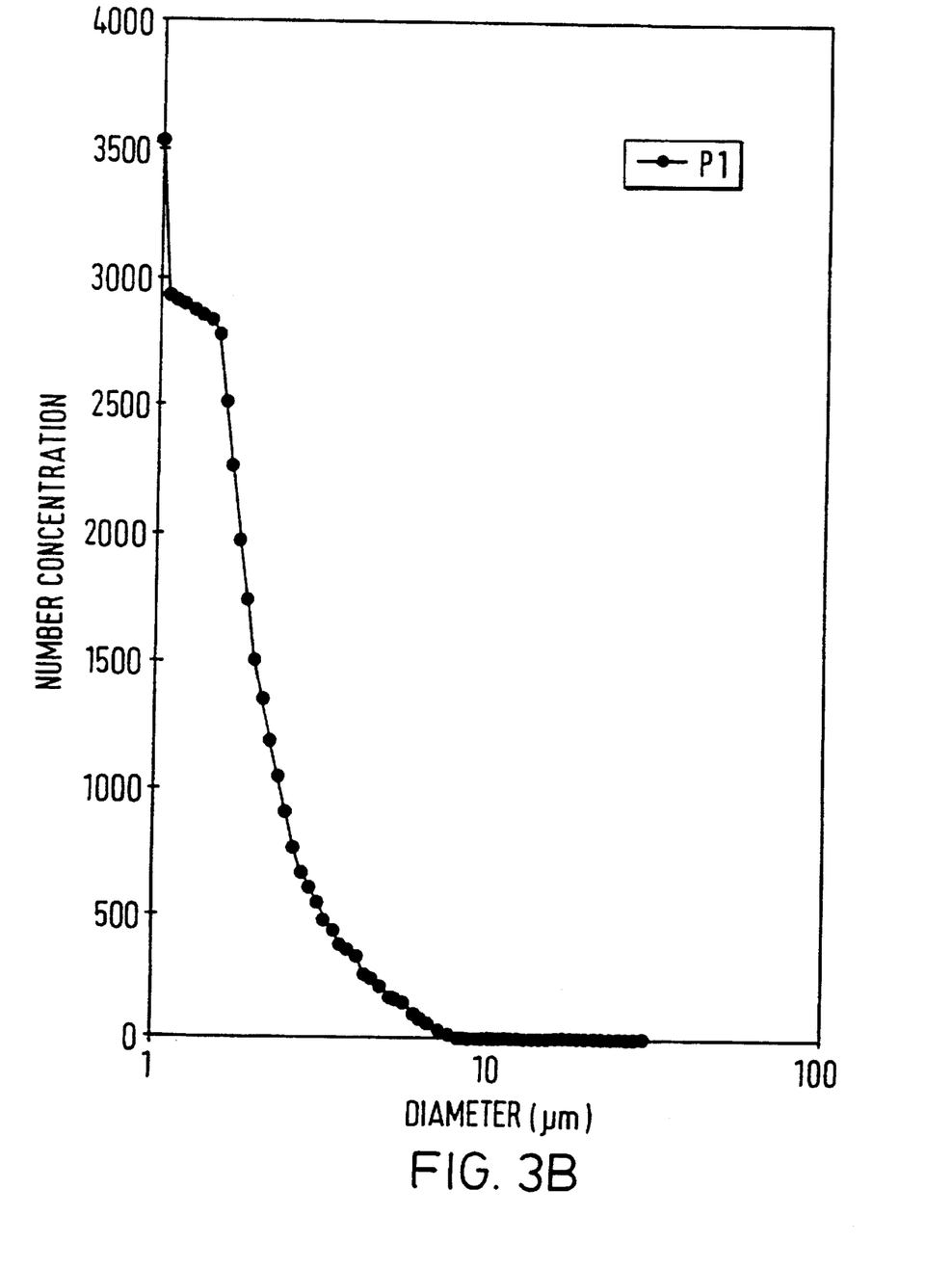
Figure 3C:
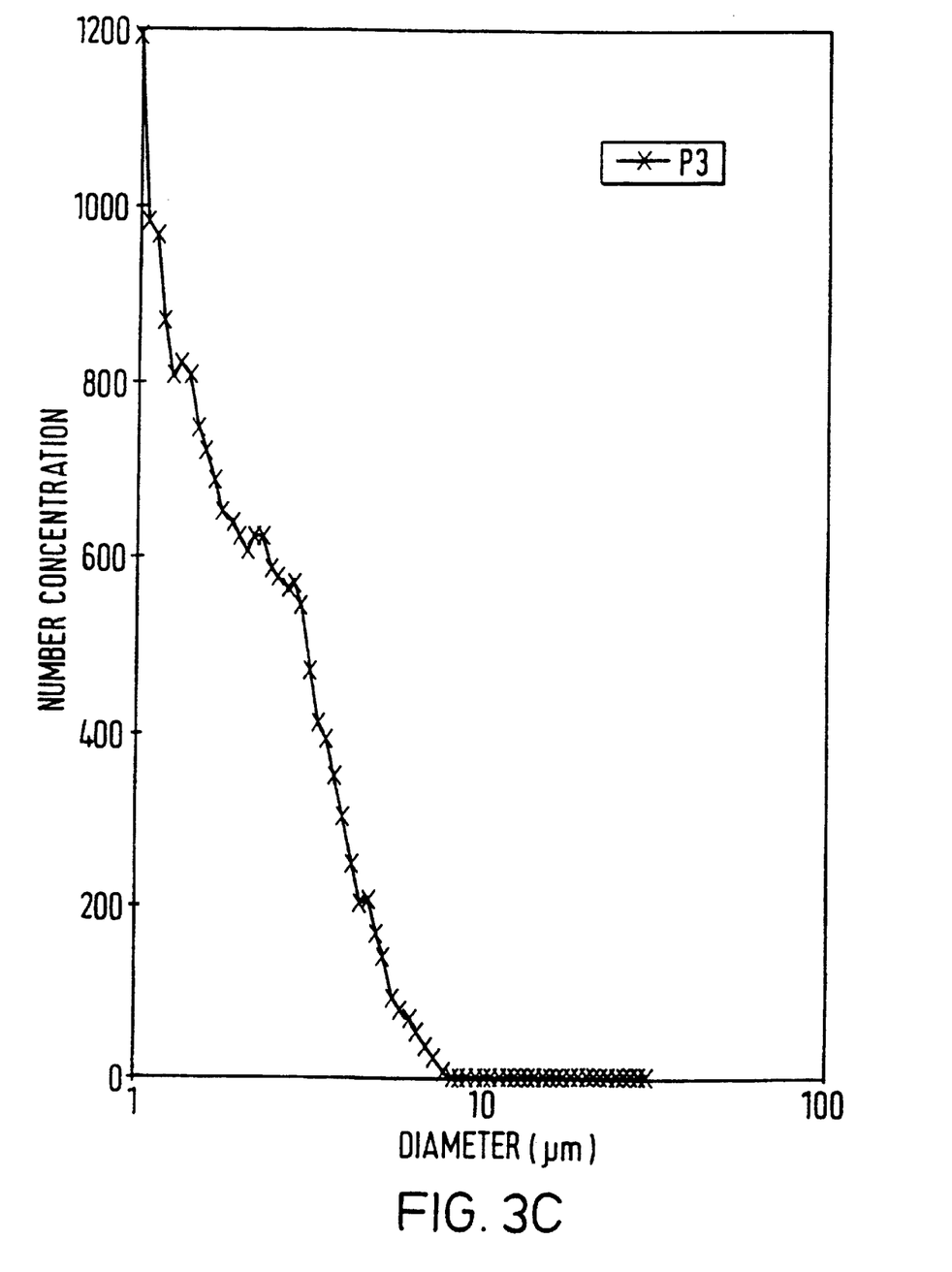
Figure 3D:
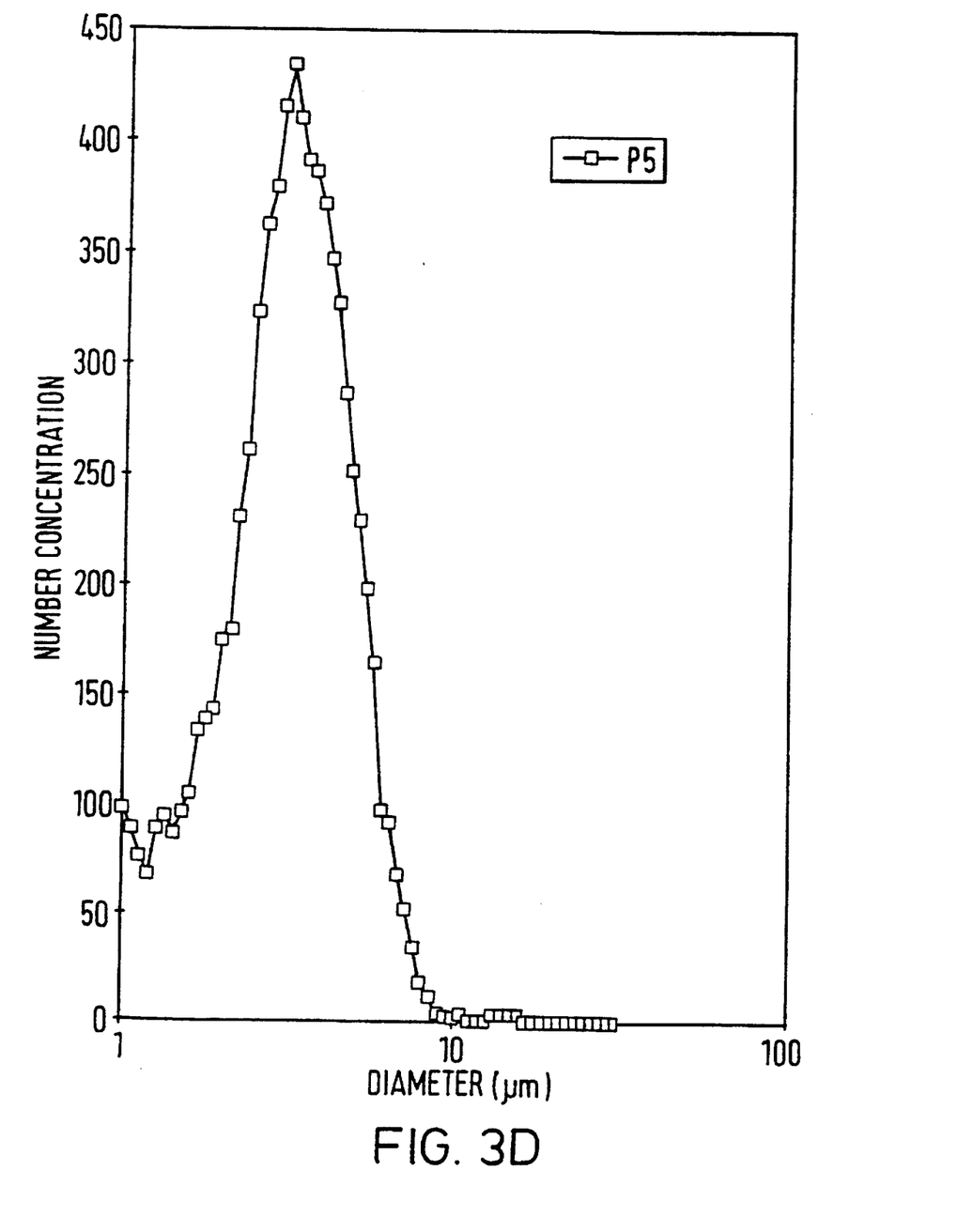
Figure 3E:
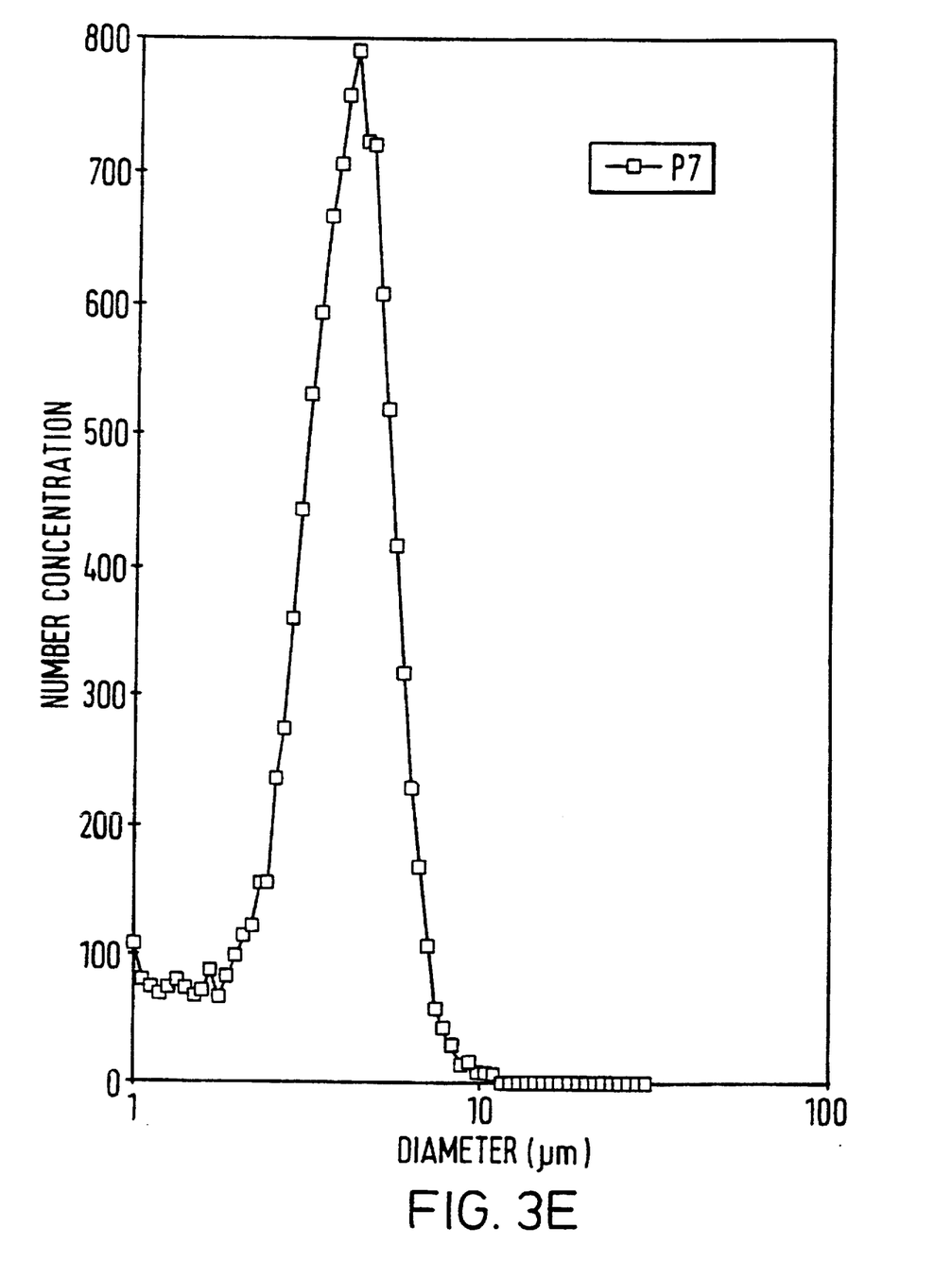
Figure 3F:
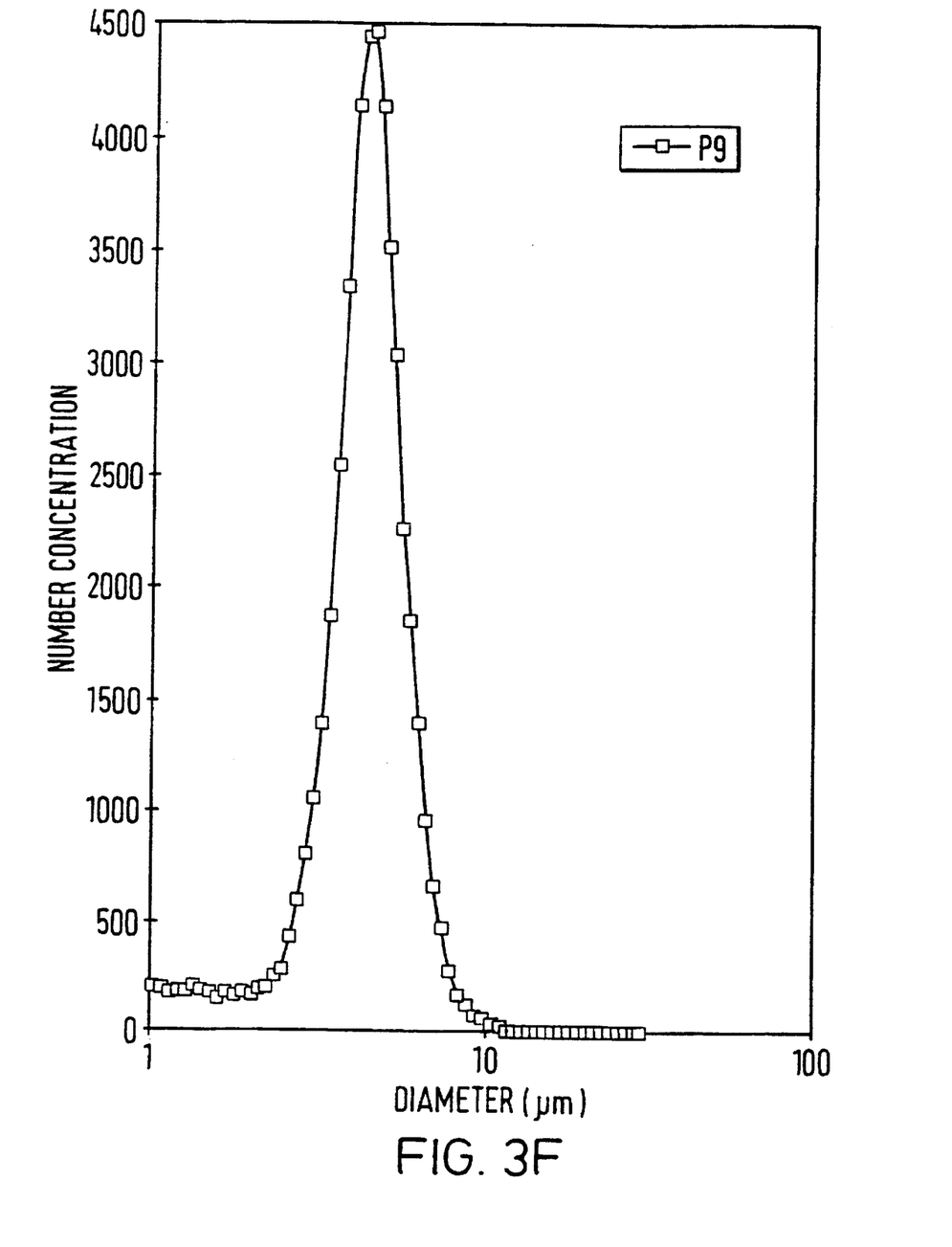

Referring to FIG. 2, there are shown diagrammatically certain stages in the separation process for a gas containing vesicular ultrasound contrast agent in an aqueous suspension medium. To achieve a mean particle size of about 3 $\mu$m a 6 cm deep suspension is stirred then allowed to settle for 200 minutes, the lower 5/6 of the suspension is drawn off to remove particles below the desired size, whereafter the fluid level is again brought up to 6 cm. FIG. 3A, FIGS. 3B to 3F and FIGS. 4 and 5 show respectively the size distributions before the process of the invention, after removal of particles smaller than 2 µm, and after further removal of particles larger than 4 µm.

EXAMPLE 1

A cylindrical flat-bottomed glass separation chamber with a total height of 80 cm and an internal diameter of 82 cm was equipped with mechanical stirring blades (as shown in FIG. 1). The chamber was filled to a height of 6 cm with 32 liters of microbubble suspension as prepared according to WO97/29783. The suspension was stirred slowly for 2 minutes, in alternate directions to obtain complete mixing, with speeds varying from 0 to 15 rpm. The suspension was allowed to settle for 200 min, and the bottom 5 cm layer was drained off through 3 outlets in the bottom into a holding tank. A connected laser size-determination apparatus revealed when a particular particle size appeared, and the outlets were closed. Water for injection (WFI) was filled into the separation chamber to 6 cm height, and stirring, settling and drainage cycles were repeated.

Aliquots of the retained particle suspensions after each cycle were tested for size distribution by Coulter Counter measurements. After 11 cycles, where particles above 2 µm had been retained, further cycles were performed to remove large particles greater than 4 µm in size, by collecting the lower layer into a receiving tank, and disposing of the upper layer. The settling time was 120 min. for these cycles at this stage. After each cycle the contents of the receiving tank were returned to the separation chamber, and WFI was added to 6 cm height.

Figure 4:
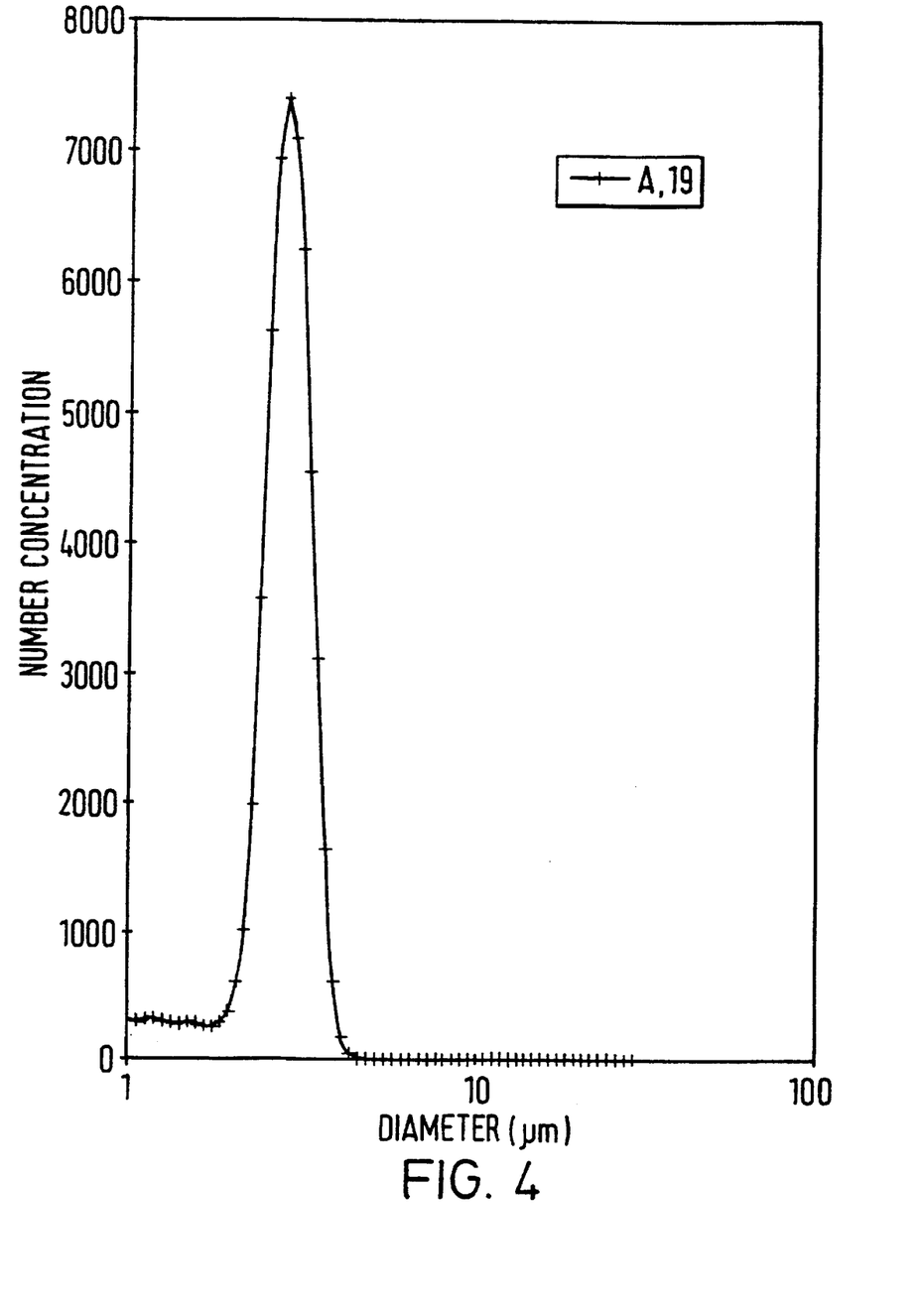
FIG. 4 is a graph showing particle size distribution following 11 two hundred minute separation cycles to remove particles below the desired size limit and a subsequent 8 one hundred and twenty minute separation cycles to remove particles above the desired size limit.
Figure 5:
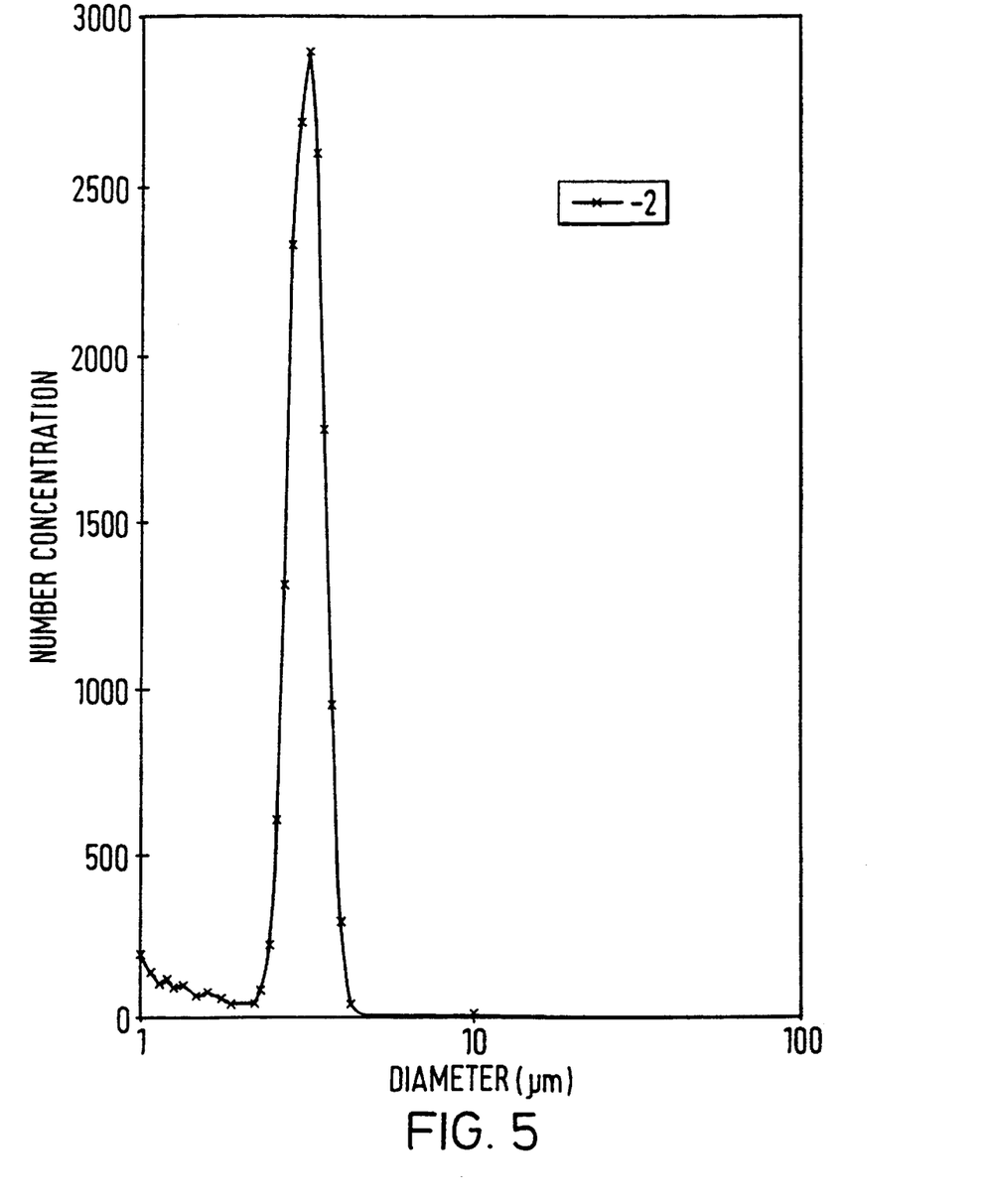
FIG. 5 is a graph showing particle size distribution following 5 two hundred minute separation cycles to remove particles below the desired size limit, then 8 one hundred and fifty minute separation cycles to remove particles below the desired size limit and then 8 one hundred minute separation cycles to remove particles above the desired size limit.

After a total of 11 cycles to remove under-sized particles, and a subsequent 8 cycles to remove oversized particles, Coulter Counter measurement revealed that 89% of the particles had a size between 2 and 4 µm (see FIG. 4).

Using the same apparatus and materials but with 5 two hundred minute separation cycles to remove particles below a desired size limit, then 8 one hundred and fifty minute separation cycles to remove particles below a desired size limit and then 8 one hundred minute separation cycles to remove particles above a desired size limit, a narrow fraction was obtained with 92% by number of particles between 2.5 and 4.5 µm and 72% between 3.0 and 4.0 µm.

What is claimed is:

1. A process for the selection from a particulate pharmaceutical product of particles of a preselected size, said process comprising
   (i) obtaining a substantially homogeneous suspension of said particulate pharmaceutical product in a fluid suspension medium which is immiscible with said product and is of different density to said product,
   (ii) carrying out a size selection procedure to set an effective lower or upper size limit on the particles in a final particulate product, and
   (iii) where required carrying out a further size selection procedure to produce a particulate product containing particles of the preselected size,
   wherein step (ii) comprises either
   (iv) allowing said suspension to settle for a predetermined period,
   (v) separating said suspension into a first and a second component in a predetermined volume ratio, said first component deriving from an upper layer of said suspension and said second component deriving from a lower layer of said suspension,
   (vi) adding further suspension medium to said first component where said medium is more dense than the pharmaceutical product or to said second component where said medium is less dense than the pharmaceutical product and mixing to produce a substantially homogeneous suspension of particulate pharmaceutical product in said fluid suspension medium, and
   (vii) repeating steps (iv) to (vi) at least once, optionally omitting the last repeat of step (vi), adding the fluid suspension medium in the repeat of step (vi) to the first component or the second component where the substantially homogeneous suspension produced in the first operation of step (vi) derives from the first component or the second component respectively, whereby to set an effective lower size limit on the particles in the final particulate product, or (viii) allowing said suspension to settle for a predetermined period, (ix) separating said suspension into a third and a fourth component in a second predetermined volume ratio, said third component deriving from an upper layer of said suspension and said fourth component deriving from a lower layer of said suspension, and retaining said third component where said medium is less dense than the pharmaceutical product or said fourth component where said medium is more dense than said product, whereby said second predetermined volume ratio is such as to set an effective upper size limit on the particles in the retained component, and optionally (x) adding further suspension medium to the non-retained component and mixing to produce a substantially homogeneous suspension, (xi) repeating steps (viii), (ix) and (x) one or more times, optionally omitting the last repeat of step (x), and collecting the retained components from step (ix) and repeats thereof.

2. A process as claimed in claim 1 wherein step (ii) is so effected as to set a lower size limit and step (iii) involves operation of steps (viii) to (xi) after a final operation of step (vi).

3. A process as claimed in claim 1 wherein the particulate pharmaceutical product obtained in step (i) is one for which an upper size limit has been set.

4. A process as claimed in claim 3 wherein the particulate pharmaceutical product obtained in step (i) comprises vesicles or emulsion droplets produced in a rotor-stator mixer.

5. A process as claimed in claim 1 further comprising concentrating the retained product.

6. A process as claimed in claim 1 further comprising drying the retained product.

7. A process for the production of a particulate pharmaceutical product, said process comprising:

(A) generating with a rotor-stator a particulate pharmaceutical product, (B) obtaining a substantially homogeneous suspension of the particulate product generated in step (A) in a fluid suspension medium which is immiscible with and of different density to the particulate product, (C) allowing said suspension to settle for a predetermined period, (D) separating said suspension into a first and a second component in a predetermined volume ratio, said first component deriving from an upper layer of said suspension and said second component deriving from a lower layer of said suspension, (E) adding further suspension medium to said first component where said medium is more dense than the pharmaceutical product or to said second component where said medium is less dense than the pharmaceutical product and mixing to produce a substantially homogeneous suspension of particulate pharmaceutical product in said fluid suspension medium, and (F) repeating steps (C) to (E) at least once, optionally omitting the last repeat of step (E), adding the fluid suspension medium in the repeat of step (E) to the first component or the second component where the substantially homogeneous suspension produced in the first operation of step (E) derives from the first component or the second component respectively, whereby to set an effective lower size limit on the particles in a final particulate product.

* * * * *